United States Patent [19]

Green et al.

[11] 4,450,174

[45] May 22, 1984

[54] DECYL QUATERNARY AMMONIUM COMPOUNDS

[75] Inventors: Harold A. Green, Havertown, Pa.; Alfonso N. Petrocci, Glen Rock; Zdzislaw W. Dudzinski, Clifton, both of N.J.

[73] Assignee: Millmaster Onyx Group, Inc., New York, N.Y.

[21] Appl. No.: 382,399

[22] Filed: May 27, 1982

[51] Int. Cl.$^3$ .................... C07C 87/30; A61K 31/14
[52] U.S. Cl. .................... 424/329; 564/291
[58] Field of Search .................... 564/291; 424/329

[56] References Cited

U.S. PATENT DOCUMENTS

| | | | |
|---|---|---|---|
| 3,054,678 | 9/1962 | Michener et al. | 424/329 |
| 3,535,380 | 10/1970 | Dudzinski et al. | 424/329 |
| 3,754,033 | 8/1973 | Shay et al. | 564/291 |
| 3,819,656 | 6/1974 | Barie et al. | 564/291 |
| 3,836,669 | 9/1974 | Dadekian | 424/329 |
| 3,880,613 | 4/1975 | Oswald et al. | 424/329 |
| 4,073,888 | 2/1978 | Snyder | 424/329 |
| 4,165,375 | 8/1979 | Berger et al. | 424/329 |

OTHER PUBLICATIONS

Angele, Chem. Abst., vol. 83, #99689e (1975).

*Primary Examiner*—James H. Reamer
*Attorney, Agent, or Firm*—Arthur A. Jacobs

[57] ABSTRACT

Quaternary ammonium salts in which either one or two of the substituents bonded to the quaternary nitrogen is a decyl radical comprising a mixture of primary 10-carbon atom branched chains.

16 Claims, No Drawings

DECYL QUATERNARY AMMONIUM COMPOUNDS

This invention relates to anti-microbial quaternary ammonium compounds, and it more particularly relates to didecyl dimethylammonium chloride, and decyl alkyl dimethylammonium chloride in which the "decyl" radical is a mixture of primary 10-carbon-atom branched chains, as distinguished from the normal or "n-decyl" straight chain.

The decyl group of this invention is derived from commercial decyl alcohol, such as is presently produced by Exxon Chemical Co. and United States Steel Company. The alcohol has a CAS number of 68551-08-6 and is, essentially, a mixture of branched primary decanols in which a straight chain has at least two branches. The preponderant component is trimethylheptanol.

Since the chemical transformations which are used to transform the decanol to the decyl substituent bonded to the quaternary nitrogen of the present compounds are comparatively mild, low energy reactions that practically preclude rearrangements, the decyl substituent on the quaternary nitrogen reflects the same radicals and distribution as is found in the starting decanol.

The quaternary ammonium salts of the present invention are prepared by the classical alkylation reaction of a tertiary amine with a primary alkyl halide. The tertiary amine is prepared by the alkylation of a secondary amine with a primary alkyl halide or by two successive alkylations of a primary amine in which the alkylating agents may be the same or different primary alkyl halides.

The quaternization of didecyl methylamine with methyl chlorides gives higher yields than the quaternization of decyl dimethylamine with decyl chloride.

Decyl n-decyl dimethylammonium chloride is prepared by quaternizing decyl n-decyl methylamine with methyl chloride.

The following examples are illustrative preparations of the compounds of this invention.

EXAMPLE 1

Decyl alcohol + HCl → decyl chloride

About 500 grams of "Exxon" decyl alcohol and about 10 grams of zinc chloride are heated to about 140° C. and dry hydrogen chloride is passed into the mixture. The effluent vapors are condensed and trapped. When the volume of the condensate remains constant (at about 60–65 ml. after about 3 hours) the reaction is halted. The organic layer in the reaction flask is washed with cold water and purified by distillation.

EXAMPLE 2

Decyl chloride + methylamine → decyl methylamine

One mol of decyl chloride is heated in an autoclave with a concentrated solution of monomethylamine in water (isopropanol or water/isopropanol mixtures may also be used), containing about 10 moles of monomethylamine, at about 110° C. for 8–10 hours. After cooling, about 1.1 moles of caustic soda is added with stirring. The organic layer is separated from the mixture, stripped of isopropanol (if present), and fractionated. The yield is about 0.75–0.80 moles of decyl methylamine.

EXAMPLE 3

Decyl chloride + decyl methylamine → didecyl methylamine

A mixture of one mole of decyl methylamine and one mole of caustic soda is heated to about 160° C. at atmospheric pressure, and one mole of decyl chloride is added slowly over a period of one hour. Heating is continued for about one more hour. The cooled organic mixture is washed with cold water and purified by distillation.

When n-decyl chloride is used instead of decyl chloride, the product is n-decyl decyl methylamine. Any other n-alkyl chloride with decyl methylamine will yield n-alkyl decyl methylamine. When n-decyl chloride is used instead of decyl chloride and n-decyl methylamine is used instead of decyl methylamine, the product is di-n-decyl methylamine.

EXAMPLE 4

Didecyl methylamine + methyl chloride → didecyl dimethylammonium chloride

One mole of didecyl methylamine in an autoclave is mixed with about an equal volume of isopropanol, or 50/50 isopropanol/water, as solvent. Then one mole of methylchloride gas (+1–2% excess) is pumped into the autoclave and the contents therein heated at about 80°–110° C. for about 12–15 hours.

Didecyl dimethylammonium chloride, the quaternary ammonium salt product, is left in solution, its concentration being about 35–50% depending upon the quantity of solvent used in the reaction.

When n-decyl decyl methylamine is used instead of didecyl methylamine, the product is n-decyl decyl dimethylammonium chloride. When di-n-decyl methylamine is used instead of didecyl methylamine, the product is di-n-decyl dimethylammonium chloride. When n-alkyl decyl methylamine is used instead of n-decyl decyl methylamine, the product is n-alkyl decyl dimethylammonium chloride.

EXAMPLE 5

Mixtures of quaternary ammonium salts were prepared as follows:
(a) 95% didecyl dimethylammonium chloride, 5% di-n-decyl dimethylammonium chloride by weight.
(b) 90% didecyl dimethylammonium chloride, 10% di-n-decyl dimethylammonium chloride, by weight.
(c) 75% didecyl dimethylammonium chloride, 25% di-n-decyl dimethylammonium chloride, by weight.

EXAMPLE 6

When methylamine was treated with an equimolar mixture of decyl chloride and n-decyl chloride by the method shown in Example 2, the product was a mixture of about 50% decyl methylamine and about 50% n-decyl methylamine. When this mixture of secondary amines was treated with the equimolar mixture of the same two alkyl halides by the method shown in Example 3, the product was a mixture of about 25% didecyl methylamine, about 25% di-n-decyl methylamine and about 50% decyl-n-decyl methylamine. When this mixture of tertiary amines was quaternized with methyl chloride by the method shown in Example 4, the product presumptively was a mixture of di-alkyl dimethylammonium chloride salts in approximately the same proportion as their parent tertiary amines, namely about 25% didecyl dimethylammonium chloride, about 25% di-n-decyl dimethylammonium chloride, and about 50% decyl-n-decyl-dimethylammonium chloride.

The antimicrobial properties of didecyl dimethylammonium chloride, di-n-decyl dimethylammonium chloride, and the three mixtures (a), (b) and (c) were investigated using the following procedure.

1. 50 ml. of solution containing the solute to be tested at test concentration was added aseptically to previously sterlized cotton-stoppered 125 ml. Erlenmeyer flasks.

2. One set of flasks containing each solute at various test concentrations was inoculated with 0.5 ml. of a 1/10 nutrient broth solution of a 24-hour nutrient broth culture of Psuedomones aeruginosa. Another set was inoculated with 0.5 ml. of a 1/10 nutrient broth solution of a 24-hour nutrient broth culture of Aerobacter aerogenes.

3. After 30 minutes, a 0.5 ml. aliquot was removed from each flask and added to 50 ml. of sterile azolectin/"Tween 80" neutralizer. "Tween 80" is a polyoxyethylene derivative of fatty acid partial esters of hexitol anhydrides which is produced by Altas Power Co., Wilmington, Del.

4. Agar plate counts were made from the aliquot solutions.

Table I shows the plate count of the products that were tested. The actual microbial count can be calculated by multiplying each number by $10^2$.

The tests were performed simultaneously in order to minimize comparative errors due to fluctuations in ambient conditions. The table shows that at concentrations of about 10 ppm. or more, the didecyl dimethyl ammonium chloride has about the same antimicrobial activity as di-n-decyl dimethylammonium chloride, and both are only slightly superior to "BTC 776".

Both di-n-decyl dimethylammonium chloride and "BTC 776" are commercially well known, potent antimicrobials. "BTC 776" is a benzalkonium quaternary manufactured by Onyx Chemical Company, Jersey City, N.J.

small amounts of certain compounds such as di-n-decyl dimethylammonium chloride, its biodegradability is increased beyond what could be expected from the sum of the contributions of the compounds.

In accordance with the above, the biodegradability of (1) didecyl dimethylammonium chloride, (2) di-n-decyl dimethylammonium chloride, and (3) physical mixtures of these two quaternary ammonium salts were determined. The extent of biodegradation was ascertained by the shake flask method. The extent of biodegradation of the mixtures was compared to the compound values calculated from the concentration and biodegradability of the pure components in the mixture.

The tests used followed those described in the following publications: *Biotransformation and Fate of Chemicals in the Aquatic Environment* (Proceedings of a Workshop Held at the University of Michigan Biological Station, Pellston, Mich., Aug. 14–18), 1979 by Alan W. Maki, Kenneth T. Dickson and John Cairn, Jr., published by the American Society for Microbiology, Washington, D.C.; *Surfactant Biodegradation*, R. D. Swisher, 1970, published by Marcel Dekker, Inc., New York, N.Y.; *A Procedure and Standard for the Determination of the Biodegradability of Alkyl Benzene Sulfonate and Linear Alkylate Sulfonate* (The Subcommitte on Biodegradation Test Methods of the Soap and Detergents Association), published by The Journal of American Oil Chemists Society, Nov. 1965 issue, Vol. 42, No. 11.

The tests were carried out in the following manner:

A mixed microbial culture obtained from sewage treatment plant activated sludge was used as the inoculant. Ten milliliters of this culture and 0.3 gm. of yeast extract were added to flasks containing 1 liter of a mineral salts medium.

The mineral salts medium consisted of the following mixture:

ammonium chloride: 3.0 gm.
dipotassium phosphate: 1.0 gm.
potassium chloride: 0.25 gm.
magnesium sulfate.$7H_2O$: 0.25 gm.
sodium bicarbonate: 0.25 gm.
$FeSO_4$: 0.002 gm.
water, q.s.: 1 liter

TABLE 1

| Concentration in p.p.m. | "BTC 776" Control | | II | | I | | $\frac{I}{II} = \frac{95\%}{5\%}$ | | $\frac{I}{II} = \frac{90\%}{10\%}$ | | $\frac{I}{II} = \frac{75\%}{25\%}$ | |
|---|---|---|---|---|---|---|---|---|---|---|---|---|
| | P.A. | A.A. | P.A. | A.A. | P.A. | A.A. | P.A. | A.A. | P.A. | A.A. | P.A. | A.A. |
| 1 | | | | | | | | | | 26.0 | | 17.0 |
| 2 | | 30.0 | | | | 8.5 | | 20.0 | | 8.5 | 11.5 | 13.5 |
| 5 | 52.5 | 20.0 | 10.0 | 0 | 5.5 | 1.5 | 199.0 | 13.5 | 92.5 | 5.0 | 3.0 | 0 |
| 5 | | | 6.5 | 0 | 0 | | 61.0 | 4.0 | 13.5 | 1.5 | 1.5 | 0 |
| 5 | | | | | | | 23.5 | 14.5 | | | | |
| 10 | 17.5 | 5.5 | 1.0 | 0 | 0 | 0 | 45.5 | 0 | 21.5 | 0 | 0 | 0 |
| 10 | 31.0 | 1.0 | 0 | 0 | 0 | | 12.5 | 0 | 1.5 | | 0 | |
| 10 | 36.5 | 9.0 | | | | | 6.0 | 0 | | | | |
| 15 | 8.0 | 1.0 | 0 | 0 | 0 | 0 | 3.0 | 0 | 0 | 0 | 0 | 0 |
| 15 | 10.0 | 0 | 0 | 0 | 0 | | 0 | | 0 | 0 | | 0 |
| 15 | 3.0 | | | | | | 0 | 0 | | | | |
| 20 | 1.5 | 0 | 0 | 0 | 0 | | 0 | 0 | 0 | 0 | 0 | 0 |
| 20 | 1.0 | 0 | 0 | 0 | | | 0 | | | | | |

P.A. = Pseudomonas Aeruginos
A.A. = Aerobacter Aerogenes
I = Didecyl Dimethylammonium Chloride
II = Di-n-decyl Dimethylammonium Chloride Although the didecyl-dimethylammonium chloride of this invention is a potent microbiocide at relatively low concentrations, as shown above, its biodegradability is much lower than di-n-decyl dimethylammonium chloride. However, when it is mixed with relatively The flasks were kept at room temperature on a gyratory shaker operating at sufficient speed to assure good aeration.

For acclimation, 10 milliliters of culture were transferred serially every three days to one liter of fresh medium containing gradually increasing concentrations of the quaternary ammonium salt that was being tested, namely, 0, 0.5, 2.0, 4.0, 6.0, 8.0, and 10.0 mg. per liter.

After 21 days of acclimation, the test was begun at the initial concentration of 10 mg. per liter of total quaternary ammonium compound.

Thereafter, a sample was drawn from the flask on the sixth day and analysed chemically for total quaternary ammonium compound concentration.

The test results are embodied in the following Table 2:

TABLE 2

INITIAL CONCENTRATION 10 mg/liter
TOTAL QUATERNARY AMMONIUM SALT
CONCENTRATION AFTER 6 DAYS (RESIDUE OF
NON-BIODEGRADED QUATERNARY AMMONIUM SALT)

| COMPOUND OR MIXTURE | FOUND | CALC'D |
|---|---|---|
| Didecyl dimethylammonium chloride (I) | 4.6 mg. | 4.6 mg. |
| Di-n-decyl dimethylammonium chloride (II) | 0.0 mg. | 0.0 mg. |
| 95% I/5% II | 2.1 mg. | 4.4 mg. |
| 90% I/10% II | 2.2 mg. | 4.1 mg. |
| 75% I/25% II | 2.0 mg. | 3.5 mg. |
| ACTUAL BIODEGRADABILITY | | |
| I | 54% | |
| II | 100% | |
| 95% I/5% II | 79% | |
| 90% I/10% II | 78% | |
| 75% I/25% II | 80% | |

All the tests shown in Table 2 were performed simultaneously in order to minimize the influence of any errors due to fluctuations in ambient conditions.

Table 2 shows the total concentration of quaternary ammonium compound not biodegraded in this test after 6 days, both for the pure materials and for three different mixtures. It also shows the compound quantities to be expected and calculated from the known biodegradability of the pure materials. For example, in the mixture of 90% didecyl dimethylammonium chloride and 10% di-n-decyl dimethylammonium chloride, a total concentration of 10 mg. per liter would contain 9.0 mg. of didecyl dimethylammonium chloride and 1.0 mg. of di-n-decyl dimethylammonium chloride. The didecyl dimethylammonium chloride would be 54% biodegraded, leaving a residue of 46% (of the 9.0 mg.) that was not biodegraded, or about 4.1 mg. The didecyl dimethylammonium chloride, being 100% biodegradable, would have no residue of non-biodegraded quaternary ammonium salt. Therefore, using the calculated amount of non-biodegraded quaternary ammonium salt in 1 liter of solution as a measure, the amount would be expected to be 4.1 mg. which is the sum of both expected residues. In fact, what was actually found was only 2.2 mg. of quaternary salt—about 50% of the expected calculated amount. Approximately the same result (about 50% of calculated amount) was found for the 95%I/5%II, and the 75%I/25%II mixtures. These results clearly show the unexpected cobiodegradation between the two quaternary ammonium salts.

The concentration of quaternary ammonium salt after biodegradation was determined by the method of M. E. Auerbach, *Industrial and Engineering Chemistry*, Analytical Edition, 15, pp. 492–3 (1944). This method was developed especially for low concentrations of quaternary ammonium salts.

As stated in the text *Biotransformation and Fate of Chemicals in the Aquatic Environment*, supra: "Practical experience has shown that chemicals which exhibit from 60% to 70% biodegradation in these laboratory tests would be better than 90% removed during biological treatment of sewage."

It should, therefore, be expected that chemicals which are biodegraded about 80% should, under practical conditions during the biological degradation of sewage, be almost completely removed during treatment.

If a minimum of 90% removal by biological treatment under practical conditions of treating sewage is taken as a standard, then it is clear that the addition of as little as about 5% of the unbranched di-n-decyl dimethylammonium quaternary salt to the branched didecyl dimethyl quaternary ammonium salts of this invention will significantly increase the biodegradability of the didecyl compound from a less than satisfactory to a very satisfactory level.

It is to be noted that not every compound that is fully biodegradable will promote the biodegradation of didecyl dimethylammonium chloride. Sucrose, for example, which, like the di-n-decyl dimethylammonium chloride, is completely biodegradable, will not influence the biodegradation of the didecyl dimethylammonium chloride. Experiment shows that the biodegradability of the branched dialkyl quaternary ammonium compound in the presence of sucrose is about 54%, whereas, as shown above, the addition of even 5% of 100% biodegradable didecyl dimethylammonium chloride raises the biodegradability of the branched dialkyl quaternary salt from about 54% to about 79% of total quaternary.

The invention claimed is:

1. A quaternary ammonium compound having the structural formula

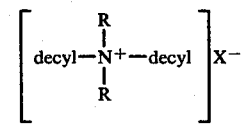

wherein R is a lower alkyl group of from 1 to 4 carbon atoms, and X is either a halogen having an atomic weight greater than 30, methosulfate or ethosulfate, the term decyl referring to a mixture of primary branched chain alkyl groups, each of which has 10 carbon atoms and consists of a straight chain having at least two branches.

2. The compound of claim 1 wherein X is chlorine.

3. The compound of claim 1 wherein R is $CH_3$.

4. The compound of claim 1 in admixture with di-n-decyl dimethylammonium halide in a ratio of between about 3:1 and about 20:1.

5. The mixture of claim 4 in aqueous solution.

6. The mixture of claim 4 wherein the di-n-decyl dimethylammonium halide is di-n-decyl dimethylammonium chloride.

7. The mixture of claim 6 in aqueous solution.

8. A method of inhibiting bacteria in an aqueous solution which comprises applying to said bacteria an inhibitorally effective amount of the compound of claim 1.

9. A method of inhibiting bacteria in an aqueous solution which comprises applying to said bacteria an inhibitorially effective amount of the compound of claim 2.

10. A method of inhibiting bacteria in an aqueous solution which comprises applying to said bacteria an inhibitorally effective amount of the compound of claim 3.

11. A method of inhibiting microorganisms in an aqueous solution which comprises applying to said microorganisms an inhibitorally effective amount of the mixture of claim 4.

12. A method of inhibiting microorganisms in an aqueous solution which comprises applying to said microorganisms an inhibitorally effective amount of the mixture of claim 6.

13. A method of increasing the biodegradability of the compound of claim 1 in aqueous solution which comprises admixing said compound with di-n-decyl dimethylammonium halide in a ratio of between about 3:1 and about 20:1.

14. The method of claim 13 wherein the di-n-decyl dimethylammonium halide is di-n-decyl dimethylammonium chloride.

15. A method of increasing the biodegradability of the compound of claim 2 in aqueous solution which comprises admixing said compound with di-n-decyl dimethylammonium halide in a ratio of between about 3:1 and about 20:1.

16. A method of increasing the biodegradability of the compound of claim 3 in aqueous solution which comprises admixing said compound with di-n-decyl dimethylammonium halide in a ratio of between about 3:1 to about 20:1.

* * * * *